(12) United States Patent
Dupps et al.

(10) Patent No.: US 9,854,964 B2
(45) Date of Patent: Jan. 2, 2018

(54) MEASUREMENT OF BIOMECHANICAL PROPERTIES IN AN OCT IMAGE

(71) Applicants: THE CLEVELAND CLINIC FOUNDATION, Cleveland, OH (US); CASE WESTERN RESERVE UNIVERSITY, Cleveland, OH (US)

(72) Inventors: William J. Dupps, Bay Village, OH (US); Matthew R. Ford, Bay Village, OH (US); Andrew M. Rollins, Highland Heights, OH (US); Michael W. Jenkins, Shaker Heights, OH (US)

(73) Assignees: The Cleveland Clinic Foundation, Cleveland, OH (US); Case Western Reserve University, Cleveland, OH (US)

( * ) Notice: Subject to any disclaimer, the term of this patent is extended or adjusted under 35 U.S.C. 154(b) by 280 days.

(21) Appl. No.: 14/700,711

(22) Filed: Apr. 30, 2015

(65) Prior Publication Data

US 2015/0313460 A1    Nov. 5, 2015

Related U.S. Application Data

(60) Provisional application No. 61/986,174, filed on Apr. 30, 2014.

(51) Int. Cl.
*A61B 3/00*    (2006.01)
*A61B 3/10*    (2006.01)
(Continued)

(52) U.S. Cl.
CPC ............ *A61B 3/102* (2013.01); *A61B 3/0025* (2013.01); *A61B 3/14* (2013.01); *A61B 5/0048* (2013.01);
(Continued)

(58) Field of Classification Search
None
See application file for complete search history.

(56) References Cited

U.S. PATENT DOCUMENTS 6,039,690 A * 3/2000 Holley .................... A61B 8/14
600/440
2003/0163044 A1   8/2003 Heimdal et al.
(Continued)

FOREIGN PATENT DOCUMENTS

EP         2656780 A1    10/2013
WO    2006024014 A2     3/2006

OTHER PUBLICATIONS

Visualization of Ultrasonically-Induced Shear Wave Propagation Using Phase Sensitive Optical Coherence Tomography. T. Nguyen et al., Feb. 2014.*

(Continued)

*Primary Examiner* — Delomia L Gilliard
(74) *Attorney, Agent, or Firm* — Tarolli, Sundheim, Covell & Tummino LLP

(57) ABSTRACT

Systems and method are provided for evaluating a biomechanical property of tissue. A shear wave generator is configured to induce a shear wave in the tissue. An optical coherence tomography (OCT) imager is configured to capture a B-scan frame of the tissue. An image processing component is configured to determine a frequency of the shear wave in the tissue from the B-scan frame of the tissue at each of a plurality of locations within the B-scan. A parameter calculation component is configured to calculate a value for the biomechanical property for a plural subset of the plurality of locations within the B-scan frame of the tissue from the determined frequency of the shear wave at each of the plural subset of the plurality of locations.

20 Claims, 3 Drawing Sheets

(51) Int. Cl.
    *A61B 3/14*    (2006.01)
    *A61B 5/00*    (2006.01)
(52) U.S. Cl.
    CPC ........ *A61B 5/0066* (2013.01); *A61B 2576/00* (2013.01)

(56) References Cited

U.S. PATENT DOCUMENTS

| | | | |
|---|---|---|---|
| 2010/0134629 A1 | 6/2010 | Lindop et al. | |
| 2012/0089019 A1* | 4/2012 | Fan ........................ | A61B 8/485 600/437 |
| 2014/0018679 A1* | 1/2014 | Chen ...................... | A61B 8/085 600/438 |
| 2015/0094579 A1* | 4/2015 | Fan ........................ | A61B 8/085 600/438 |

OTHER PUBLICATIONS

Nguyen, et al. "Visualizing ultrasonically induced shear wave propagation using phase-sensitive optical coherence tomography for dynamic elastography." Optics letters 39.4 (2014): 838-841.
Parker, et al. "Techniques for elastic imaging: a review." Engineering in Medicine and Biology Magazine, IEEE 15.6 (1996): 52-59.
Sun, Cuiru, et al "Optical coherence elastography: current status and future applications." Journal of biomedical optics 16.4 (2011): 043001-043001.
Ford, et al. "Method for optical coherence elastography of the cornea." Journal of biomedical optics 16.1 (2011): 016005-016005.
International Search Report and Written Opinion for PCT/US2015/028505, mailed Jul. 16, 2015, pp. 1-13.

* cited by examiner

MEASUREMENT OF BIOMECHANICAL PROPERTIES IN AN OCT IMAGE

RELATED APPLICATION

This application claims priority to U.S. Provisional Patent Application No. 61/986,174, filed Apr. 30, 2014. The entire contents of this application are hereby incorporated by reference.

TECHNICAL FIELD

This invention relates to imaging systems, and more particularly, to the measurement of biomechanical properties in an OCT image.

BACKGROUND OF THE INVENTION

The measurement and understanding of corneal biomechanical properties is an important area of study to improve detection of corneal disease states, and to better understand and alter corneal shape and refraction. Diseases hypothesized to involve a significant disorder of biomechanical strength and drastic alterations to corneal shape include pellucid marginal degeneration, keratoconus, and keratoglobulus. The emergence of corneal collagen crosslinking as a treatment for ectactic corneal disease by stiffening the stroma is a promising treatment, but the mechanical effects have not been completely characterized, largely due to a lack of tools for measuring corneal mechanical properties.

SUMMARY OF THE INVENTION

In accordance with an aspect of the present invention, a system is provided for evaluating a biomechanical property of tissue. A shear wave generator is configured to induce a shear wave in the tissue. An optical coherence tomography (OCT) imager is configured to capture a B-scan frame of the tissue. An image processing component is configured to determine a frequency of the shear wave in the tissue from the B-scan frame of the tissue at each of a plurality of locations within the B-scan. A parameter calculation component is configured to calculate a value for the biomechanical property for a plural subset of the plurality of locations within the B-scan frame of the tissue from the determined frequency of the shear wave at each of the plural subset of the plurality of locations.

In accordance with another aspect of the present invention, a non-transitory computer readable medium stores instructions for evaluating a biomechanical property of tissue from an image frame representing the tissue received from an OCT imager. The instructions include an OCT interface configured to receive the image frame from the OCT imager, and a shear wave generator interface configured to drive a shear wave generator at a desired frequency. An image processing component is configured to determine, from the image frame of the tissue, a frequency of the shear wave at each of a plurality of locations within the image frame. The image processing component is configured to process phase differences between adjacent pixels in the image frame to produce a Doppler image of the tissue and includes a discrete Fourier transform component configured to calculate an instantaneous frequency for each of the plurality of locations. A parameter calculation component is configured to calculate a value for the biomechanical property for a plural subset of the plurality of locations within the image frame of the tissue from the determined instantaneous frequency of the shear wave at each of the plural subset of the plurality of locations.

In accordance with yet another aspect of the present invention, a method is provided for evaluating a biomechanical property of tissue. A shear wave is induced in the tissue. An OCT image of the tissue is captured, and a Doppler image is generated from the OCT image. An instantaneous frequency of the shear wave in the tissue is determined from the Doppler image at each of a plurality of locations within the Doppler image via a discrete Fourier transform. A value for the biomechanical property is calculated for a plural subset of the plurality of locations from the determined frequency of the shear wave at each of the plural subset of the plurality of locations.

BRIEF DESCRIPTION OF THE DRAWINGS

The features, objects, and advantages of the hybrid qubit assembly will become more apparent from the detailed description set forth below when taken in conjunction with the drawings, wherein.

DETAILED DESCRIPTION

Figure 1:
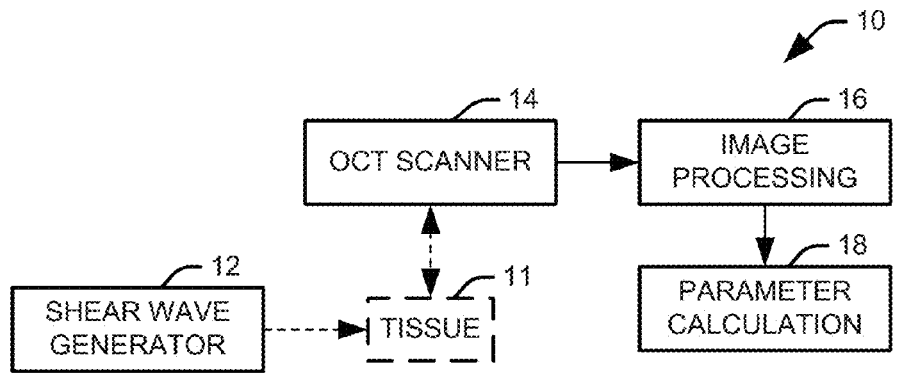
FIG. 1 illustrates a system for evaluating a biomechanical property of tissue.

FIG. 1 illustrates a system 10 for evaluating a biomechanical property of tissue. The illustrated system 10 induces a shear wave within the tissue 11 and measures the velocity of the shear wave at locations within the tissue to estimate the material properties of the tissue. To this end, the system 10 includes a shear wave generator 12 configured to induce a shear wave in the tissue 11. It will be appreciated that the shear wave generator can be configured to be placed in physical contact with the tissue 11 to be evaluated, in physical contact with surrounding tissue, or separated from the tissue by a medium that accurately conducts acoustic waves, such as air. In one example, the shear wave generator 12 is implemented as a set of piezo-electric bimorph and piezo electric stacks driven by an appropriate control system. It will be appreciated, however, that the shear wave generator 12 can be implemented as any transducer configured to produce mechanical waves within the tissue 11, including ultrasound transducers.

An optical coherence tomography (OCT) imager 14 is configured to capture a B-scan frame of the tissue 11 during the inducement of the shear wave. Specifically, the OCT imager 14 is configured to capture the B-scan frame within a plane normal to the motion of the wave, such that the wave propagates within the captured plane. The captured B-scan frame is then provided to an image processing component 16 configured to determine a frequency of the shear wave in the tissue 11 from the B-scan frame of the tissue at each of a plurality of locations within the B-scan. It will be appreciated that the image processing component 16 can be part of the software, firmware, or circuitry associated with the OCT imager 14, a completely standalone component comprising either or both of dedicated hardware and software or firmware executed by an associated processor, or distributed across the OCT imager 14 and a standalone component.

In one example, the image processing component 16 is configured to process phase differences between adjacent A-lines in the B-scan frame to produce a Doppler image of the tissue. The image processing component then analyzes the Doppler image as to determine an instantaneous frequency a plurality of locations. To this end, a discrete Fourier transform algorithm, such as a fast Fourier transform, can be applied. For example, for each location, the image processing component 16 can calculate the instantaneous frequency from phase values within a one-dimensional window that includes the location. In one implementation, the one-dimensional window can have a width of between two hundred pixels and eight hundred pixels.

A parameter calculation component 18 is configured to calculate a value for the biomechanical property for some or all of the plurality of locations within the B-scan frame of the tissue 11, representing a plural subset of the plurality of locations, from the determined frequency of the shear wave the evaluated locations. It will be appreciated that the plural subset can be a proper subset or coextensive with the plurality of locations. In one implementation, the parameter calculation component is configured to calculate the shear modulus, G, for each of the plural subset of the plurality of locations, as:

$$G = \sqrt{\frac{Vf_0}{\rho(f - f_0)}},$$

where V is the velocity of a sample arm scanner associated with the OCT imager, $f_0$ is a true frequency of the shear wave, f is the measured frequency of the shear wave at the location, and $\rho$ is the density of the tissue.

In the illustrated system 10, the shear wave generator 12 can be the only significant source of relative motion between the tissue 11 and the OCT imager 14. Accordingly, the image processing component 16 determines a frequency of the shear wave generated by this single source, as opposed to an interference wave generated by multiple sources. This implementation allows for a significant simplification of the system, as it eliminates at least one moving part and removes the necessity of synchronizing multiple sources of perturbation.

Figure 2:
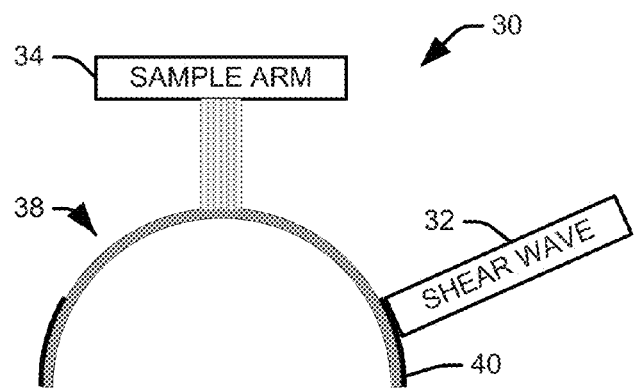
FIG. 2 is a schematic diagram of one example application of a system for evaluating a biomechanical property of tissue.

FIG. 2 is a schematic diagram of one example application of a system 30 for evaluating a biomechanical property of tissue. In the illustrated implementation, the system 30 evaluates biomechanical properties of corneal tissue, specifically one or both of the shear modulus and Young's modulus. The system 30 includes a shear wave generator 32, an OCT system, with the illustrated component being the sample arm 34 associated with the OCT system, and a computer for data capture and analysis (not shown). The shear wave generator 32 is positioned on or near the eye 38 and configured to induce a shear wave within the eye tissue. In one example, the shear wave generator 32 is positioned lower eyelid 40 roughly in line with the vertical meridian running through the pupil. The OCT scan was then run in the same vertical meridian.

In the illustrated implementation, the shear wave generator 32 includes a piezo-electric bimorph and piezo electric stacks driven by an arbitrary function generator and a one hundred and fifty volt amplifier. In the illustrated example, the OCT images are captured with the plane of the image starting from the shear wave generator 32 and running in a line directly away from the shear wave generator. This ensures that the wave propagation aligns correctly with the image. In the illustrated implementation, the shear wave generator 32 is illustrated as in contact with the eye lid 40. It will be appreciated, however, that the shear wave generator 32 could be positioned directly on the cornea or spaced from the cornea by a non-tissue medium such as air. In the illustrated implementation, the shear wave generator 32 is configured to provide a surface deformation of less than four micrometers to ensure compliance with FDA safety protocols. It will be appreciated, however, that amplitudes significantly less than four micrometers can be successfully used in measuring biomechanical properties.

Figure 3:
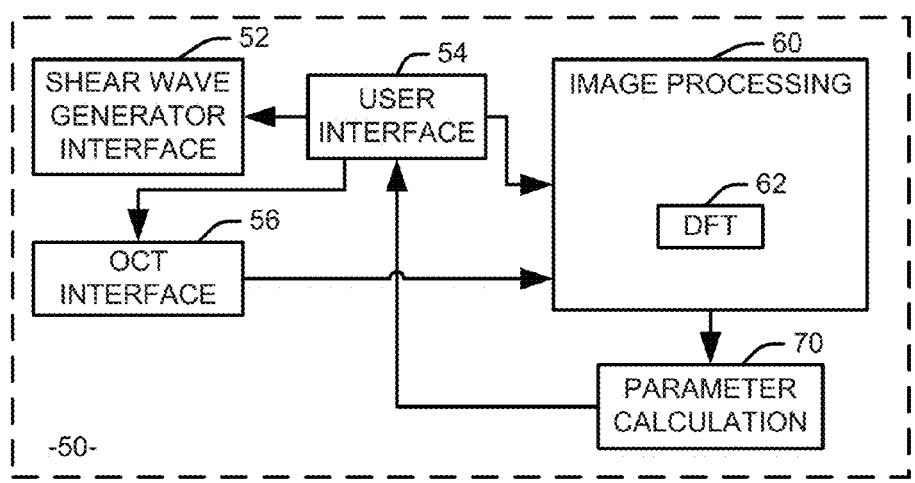
FIG. 3 illustrates an example implementation of a system for evaluating a biomechanical property of tissue in conjunction with a shear wave generator and an OCT system.

FIG. 3 illustrates an example implementation of a system 50 for evaluating a biomechanical property of tissue in conjunction with a shear wave generator and an OCT system. In the illustrated implementation, the system 50 is implemented as machine executable instructions stored on one or more non-transitory computer media. The medium would be operatively connected to at least one processor (not shown) to execute the instructions and carry out the function of the system 50. It will be appreciated, however, that the illustrated system could be implemented as dedicated hardware or a mix of dedicated hardware and software or firmware components. It will be appreciated that, in the illustrated system, a standard OCT system can be used without modification. In such a case, some of the functions of the OCT interface 56 and the user interface 54 may be implemented at the OCT system.

The system 50 includes a shear wave generator interface 52 configured to communicate instructions to a shear wave generator (not shown) associated with the system. For example, the shear wave generator interface 52 can drive the shear wave generator to provide a shear wave at a particular frequency. In one implementation, the frequency range can be varied from ten hertz to forty kilohertz, and the inventors have determined that shear wave frequencies from five hundred hertz to two kilohertz work well with traditional OCT systems. In an example implementation, a frequency of one kilohertz can be used. It will be appreciated that the frequency and any other relevant parameters for the shear wave generator can be set by a user at an associated user interface 54.

An OCT interface 56 is configured to receive an image from the OCT system and facilitate configuration of the OCT system, for example, via the user interface 54. In one implementation, the OCT system can be configured to utilize a one hundred kilohertz A-line rate swept source to provide an axial resolution of around six micrometers in tissue and a spot size of approximately twenty-five micrometers. The OCT image received at the OCT interface 56 is then provided to an image processing component 60.

The image processing component 60 is configured to determine, from the image frame of the tissue, a frequency of the shear wave at each of a plurality of locations within the image frame. To this end, in the illustrated implementation, the image processing component 60 is configured to apply an averaging threshold filter to segment the image to locate a region of interest and provide a Doppler image of at least the region of interest. For example, the Doppler image can be generated by processing the phase difference between adjacent a-lines in the image and applying a two-dimensional median filter to reduce the noise in the resultant image.

The image processing component 60 can include a discrete Fourier transform (DFT) component 62 configured to determine the instantaneous frequency at each of a plurality of locations. In the illustrated implementation, the instantaneous frequency of each pixel within the frame was determined by applying a one dimensional FFT window across the lateral aspect of the image. While the ideal window size can vary according to the sampling and method used to estimate the frequency, in the illustrated implementation, a window between two hundred and eight hundred pixels in size can be used. In one example, the window size used was five hundred pixels, corresponding to five hundred micrometers.

In the illustrated implementation, the image processing component 60 identifies the frequency peak using a combination of zero padding to several hundred thousand points and using a bin error estimator. The bin error estimator is added to the calculated peak from the Fourier transform to correct for bin size in the results. This technique reduces the processing time and increase the accuracy of the frequency peak measurement, although it will be appreciated that other techniques for identifying the frequency peak can be used. In one example, a Blackman-Harris window is applied to the data and the appropriate correction utilized in the bin error estimator. In that example, the Blackman-Harris window is used because of its sharp peak and the fact that phase linearity is not important in ensuring the correct identification of the largest frequency component. The bin error correction, δ, is calculated as:

$$\delta = \text{Re}\left[\frac{Q(X_{k-1} - X_{k+1})}{(2X_k + X_{k-1} + X_{k+1})}\right] \qquad \text{Eq. 1}$$

where Q is an offset parameter for the Blackman-Harris window, $X_{k-1}$ is the point prior to the calculated peak, $X_k$ is the calculated peak, and $X_{k+1}$ is the point after the calculated peak.

Once the frequency at each of the plurality of locations has been determined, a parameter calculation component 70 is configured to calculate a value for the biomechanical property for some or all pf the plurality of locations from the determined instantaneous frequency of the shear wave. To this end, a true speed, C, of the wave within the tissue can be determined as:

$$C = V\frac{f_0}{f - f_0} \qquad \text{Eq. 2}$$

where V is the velocity of a sample arm scanner associated with the OCT imager, $f_0$ is the known frequency of the shear wave, and f is the measured frequency of the shear wave.

In the illustrated implementation, the parameter calculation component 70 can used the determined speed of the sheer wave to calculate either or both of Young's modulus and a shear modulus at some of all of the plurality of locations. A shear modulus, G, can be calculated, as:

$$G = \sqrt{\frac{C}{\rho}} = \sqrt{\frac{Vf_0}{\rho(f - f_0)}} \qquad \text{Eq. 3}$$

where V is the velocity of the sample arm scanner associated with the OCT imager, $f_0$ is a true frequency of the shear wave, f is the measured frequency of the shear wave at the location, and ρ is the density of the tissue.

For a homogenous, isotropic material, Young's modulus, E, can be calculated as:

$$E = 3\sqrt{\frac{C}{\rho}} = 3\sqrt{\frac{Vf_0}{\rho(f - f_0)}} \qquad \text{Eq. 4}$$

where V is the velocity of a sample arm scanner associated with the OCT imager, $f_0$ is a true frequency of the shear wave, f is the measured frequency of the shear wave at the location, and ρ is the density of the tissue.

It is not always appropriate to make the assumption of a homogeneous isotropic material, especially in the cornea. However, given the spatial extent of the acoustic wave at low frequencies, such as frequencies below two kilohertz, this is not a bad assumption. This calculation may require modification for higher frequency waves with corresponding smaller spatial extent.

The calculated values can be provided to the user at the user interface 54 or provided to a modelling component (not shown) for use in modelling the imaging tissue. Such a modelling component can be found, for example, in U.S. Pat. No. 8,346,518, which is hereby incorporated by reference. The illustrated system would provided the biomechanical parameters utilized by this system to provided a patient specific model of corneal tissue.

The illustrated system 50 measures the speed of a shear wave in both in a single OCT frame, and is compatible with a standard OCT system. The high speed nature of this technique allows for rapid acquisition of material properties with OCT resolution. This has important implications for the areas of corneal refractive surgery and disease detection. Further, as mentioned previously, the information obtained here can be used as an input to mechanical models of tissue, such as corneal tissue, to further refine their results and predictive power. Because the technique requires only a single frame for analysis, three dimensional measurements can be easily designed based on the location of the shear wave device. Additionally, there is no need for complicated timing sequences between the OCT acquisitions and the shear wave modulator. Since it only requires a single shear wave, rather than two or more, the in vivo application can be done with very low power and very little tuning is necessary to ensure proper wave propagation.

Figure 4:
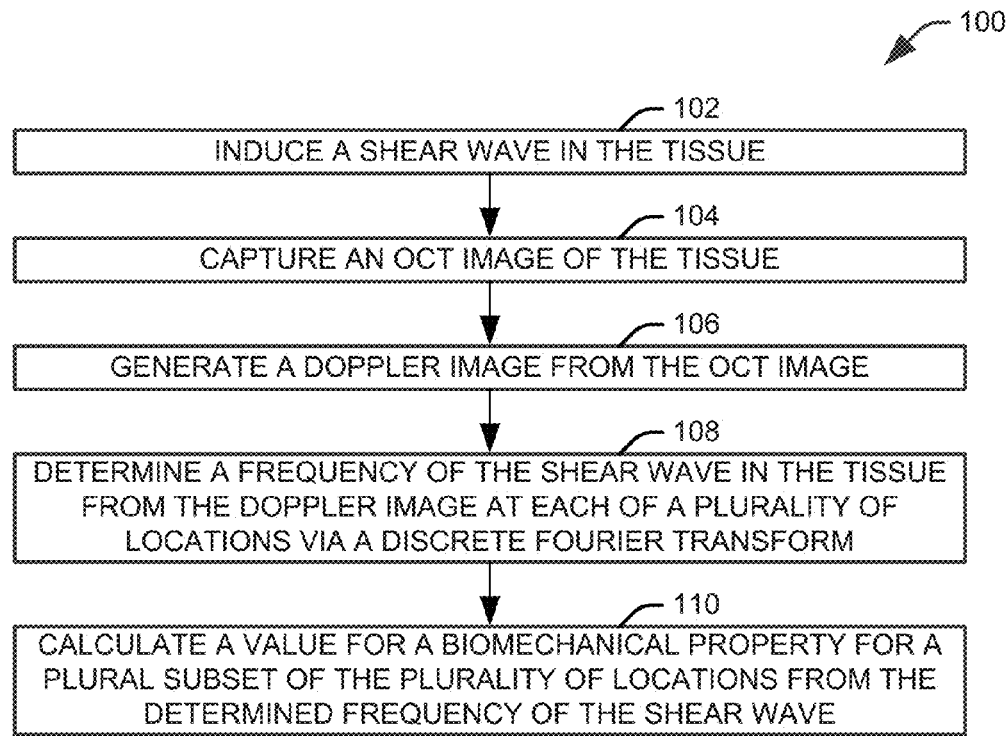
FIG. 4 illustrates a method for evaluating a biomechanical property of tissue.

In view of the foregoing structural and functional features described above, a method in accordance with an aspect of the present invention will be better appreciated with reference to FIG. 4. While, for purposes of simplicity of explanation, the method of FIG. 4 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

FIG. 4 illustrates a method 100 for evaluating a biomechanical property of tissue. At 102, a shear wave is induced in the tissue. In one implementation, the shear wave is induced in the tissue via a single shear wave source, such that an initial frequency, that is, the frequency absent the effects of any material properties of the tissue, of any shear wave measured in the method 100 is equal to the frequency at which the single shear wave source is driven. At 104, an OCT image of the tissue is captured, and a Doppler image is generated from the OCT image at 106.

At 108, an instantaneous frequency of the shear wave in the tissue from the Doppler image is determined at each of a plurality of locations within the Doppler image via a discrete Fourier transform. In one implantation, the instantaneous frequency at each of the plurality of locations from only the Doppler image and a known frequency of the induced shear wave, such that no additional image frames are utilized. At 110, a value for the biomechanical property is calculated for a plural subset of the plurality of locations from the determined frequency of the shear wave at each of the plural subset of the plurality of locations. It will be appreciated that the plural subset can be proper or coextensive with the plurality of locations. In one implementation, one or both of Young's modulus and a shear modulus can be determined at each of the plural subset of locations.

Figure 5:
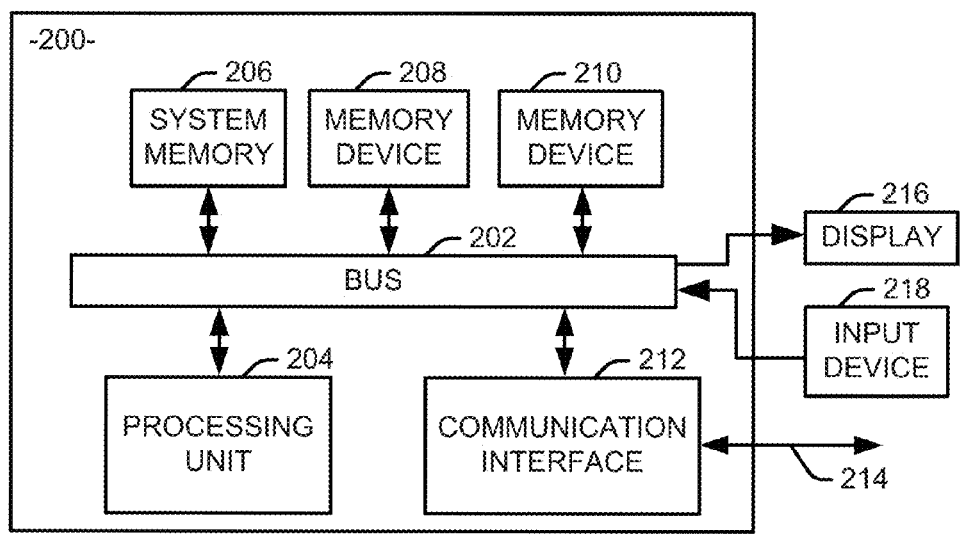
FIG. 5 is a schematic block diagram illustrating an exemplary system of hardware components capable of implementing examples of the systems and methods disclosed herein.

FIG. 5 is a schematic block diagram illustrating an exemplary system 200 of hardware components capable of implementing examples of the systems and methods disclosed herein, such as the imaging and biomechanical analysis system described previously. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard, touch screen, and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of an imaging system in accordance with the present invention. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can include a single medium or multiple, operatively-connected media operating in concert.

Figure 6:
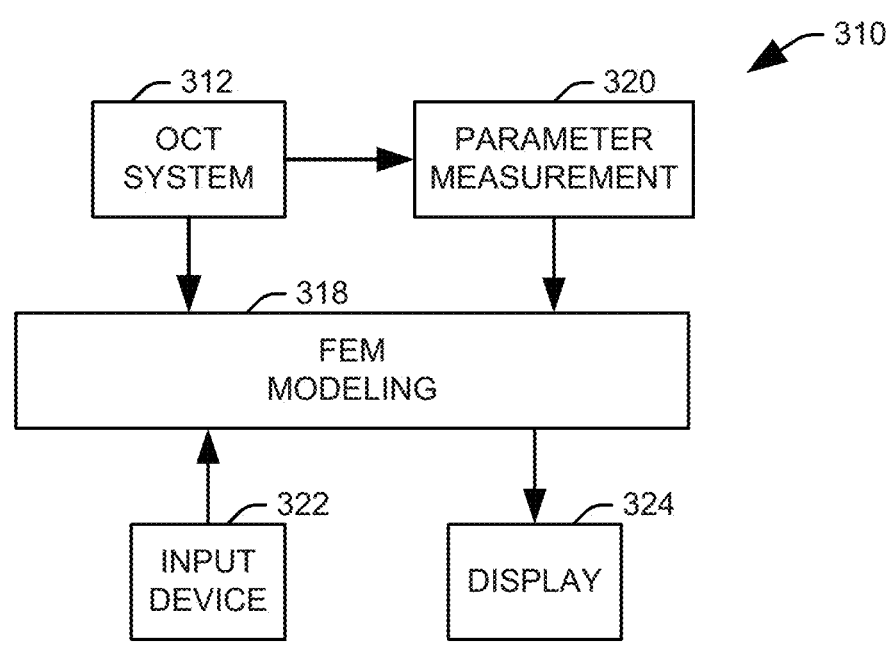
FIG. 6 illustrates a system for generating a predicted condition of a patient's eye in view of a proposed therapeutic procedure based on a biomechanical model of the eye.

FIG. 6 illustrates a system 310 for generating a predicted condition of a patient's eye in view of a proposed therapeutic procedure based on a biomechanical model of the eye. The system 310 utilizes a whole eye representation of the eye to determine the forces and stresses applied to the corneal tissue. Accordingly, predicted shape, specifically the corneal shape, is influenced by properties of portions of the eye other than the cornea, sclera, and the cornea-sclera boundary (i.e., the corneal limbus). The system 310 comprises an OCT scanner 312 that is configured to provide a representation of a patient's eye. The determined images can be supplemented by additional values, such as a measured corneal topography and a determined axial length of the eye. To this end, the system 310 can further include, for example, an ultrasound imaging device (not shown) or a partial coherence interferometer arrangement (not shown), for determining the axial length. It will be appreciated that, while the system 310, focuses on the effects of surgical and therapeutic intervention on the corneal and the resulting visual effects, the representation of the patient's eye can further include each of the sclera, the lens, the zonules, the choroid, the retina, the iris and, the ciliary body of the eye.

The images provided by the OCT scanner 312 can be digitized and processed as to obtain an overall geometry of the eye. For example, the images can be filtered and one or more edge detection algorithms can be utilized to determine the boundaries of the various tissue layers. Once the boundaries of the various tissue components is established, the processed image data can be provided to a finite element modeling (FEM) component 318 that establishes a finite element model of the ocular tissue according to the determined geometry of the eye and one or more biomechanical parameters, which can include parameters such as Poisson's ratio and Young's modulus, as well as non-linear measures of elasticity, such as hysteresis, creep, stress relaxation, and a strain dependent function for Young's modulus, for each of the tissue types.

In the illustrated implementation, one or more biomechanical parameters specific to the patient are determined at a biomechanical parameter measurement system 320, such as the system 10 for evaluating a biomechanical property of tissue in FIG. 1. To this end, the OCT scanner 312 can provide data to the biomechanical parameter measurement system 320 to allow for evaluation of a shear wave induced in the eye by shear wave generator associated with the biomechanical parameter measurement system 320, as described previously. In this implementation, the data from the imaging system 312 and the biomechanical parameter measurement system 320 can be used at the FEM component 318 to generate the finite element model of the cornea, including displacements and strains on the corneal tissue from other portions. Alternatively, the biomechanical parameter measurement system 320 can provide the biomechanical parameters as spatially varying functions of one or more parameters across a portion of the eye (e.g., the cornea and sclera), with the finite element modeling component 318 utilizing the functions to model the biomechanical properties of the tissue.

Once a geometry for the eye and biomechanical parameters for the tissue have been established, individual parameters for the finite elements comprising the model can be altered by a user at an input device 322, such as to simulate a therapeutic intervention. For example, a user can alter one or both of the thickness or biomechanical properties of the model for a given region of tissue as to simulate a therapeutic procedure, such as refractive surgery or collagen stiffing of the corneal tissue. The altered model can then be reconciled to calculate an overall shape of the eye, with an emphasis on the cornea and sclera. From the determined shape, one or more optical parameters, such as optical power values and Zernike polynomials characterizing the shape of the cornea, can be determined and provided to the user, along with the calculated shape of the eye at a display 324.

In one implementation, the FEA model can be reduced to a model of the cornea and sclera, with the forces exerted by the other tissue layers represented as an external force on the cornea tissue. Accordingly, while this reduced model does not directly incorporate extracorneal tissue into the model, known effects that have been characterized from the whole eye model can be incorporated into the model to maintain the influence of structures other than the cornea and sclera on the corneal shape. It will be appreciated that the force representing the effects of the extracorneal structures can be determined according to specific characteristics of a patient's eye, including known geometric properties derived from the image data as well as any biomechanical properties of the extracorneal tissue determined at the biomechanical parameter measurement system 320.

Further, in accordance with an aspect of the present invention, the determined model can be corrected for intraocular pressure (IOP) such that the changes applied to simulate a therapeutic procedure are applied to an "inverse model" that is adjusted to reflect the condition of the patient's eye absent intraocular pressure. Once the changes have been applied, the reconciled model can be adjusted to include an appropriate value for the patient for intraocular pressure. It will be appreciated that the influence of intraocular pressure on the corneal shape can be significant, and has been determined, through use of a whole eye model in accordance with an aspect of the present invention, to depend greatly on the material properties of the cornea. Accordingly, the results of a therapeutic intervention, particularly refractive surgery, can vary significantly according to the stiffness of the corneal tissue and the intraocular pressure of the eye.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A system for evaluating a biomechanical property of tissue, comprising:

a shear wave generator configured to induce a shear wave in the tissue;

an optical coherence tomography (OCT) imager configured to capture a B-scan frame of the tissue;

an image processing component configured to determine a frequency of the shear wave in the tissue from the B-scan frame of the tissue at each of a plurality of locations within the B-scan; and a parameter calculation component configured to calculate a value for the biomechanical property for a plural subset of the plurality of locations within the B-scan frame of the tissue from the determined frequency of the shear wave at each of the plural subset of the plurality of locations.

2. The system of claim 1, wherein the image processing component is configured to process phase differences between adjacent A-scans in the B-scan frame to produce a Doppler image of the tissue.

3. The system of claim 2, the image processing component comprising a discrete Fourier transform component configured to analyze the Doppler image as to determine an instantaneous frequency at each of the plural subset of the plurality of locations.

4. The system of claim 3, wherein the discrete Fourier transform component is configured to, for each location of the plural subset, calculate the instantaneous frequency from phase values within a one-dimensional window including the location.

5. The system of claim 4, wherein the one-dimensional window has a width of between two hundred pixels and eight hundred pixels.

6. The system of claim 1, wherein the OCT imager is configured to capture the B-scan image such that the plane of the B-scan image starts at the shear wave generator and proceeds in a line directly away from the shear wave generator.

7. The system of claim 1, wherein the tissue is corneal tissue, and the shear wave generator is configured to engage an eye lid.

8. The system of claim 1, the parameter calculation component being configured to calculate the shear modulus, G, for each of the plural subset of the plurality of locations, as:

$$G = \sqrt{\frac{Vf_0}{\rho(f-f_0)}},$$

where V is the velocity of a sample arm scanner associated with the OCT imager, $f_0$ is a true frequency of the shear wave, f is the measured frequency of the shear wave at the location, and $\rho$ is the density of the tissue.

9. The system of claim 1, wherein the shear wave generator is the only significant source of relative motion between the tissue and the OCT imager.

10. The system of claim 1, wherein the shear wave generator is configured to induce the shear wave such that a frequency of the shear wave is between ten hertz and forty kilohertz.

11. The system of claim 1, wherein the shear wave generator is configured to directly engage the tissue to induce the shear wave.

12. The system of claim 11, wherein the shear wave generator comprises a piezo-electric bimorph and piezo electric stacks.

13. The system of claim 1, wherein the shear wave generator is an ultrasound transducer.

14. The system of claim 1, wherein the plural subset of the plurality of locations is a proper subset.

15. A non-transitory computer readable medium storing instructions for evaluating a biomechanical property of tissue from an image frame representing the tissue received from an optical coherence tomography (OCT) imager, the instruction comprising:
   an OCT interface configured to receive the image frame from the OCT imager;
   a shear wave generator interface configured to drive a shear wave generator at a desired frequency;
   an image processing component configured to determine, from the image frame of the tissue, a frequency of the shear wave at each of a plurality of locations within the image frame, the image processing component being configured to process phase differences between adjacent pixels in the image frame to produce a Doppler image of the tissue and comprising a discrete Fourier transform component configured to calculate an instantaneous frequency for each of the plurality of locations; and
   a parameter calculation component configured to calculate a value for the biomechanical property for a plural subset of the plurality of locations within the image frame of the tissue from the determined instantaneous frequency of the shear wave at each of the plural subset of the plurality of locations.

16. The non-transitory computer readable medium of claim 15, the parameter calculation component being configured to calculate the Young's modulus, E, for each of the plural subset of the plurality of locations, as:

$$E = 3\sqrt{\frac{Vf_0}{\rho(f - f_0)}},$$

where V is the velocity of a sample arm scanner associated with the OCT imager, $f_0$ is a true frequency of the shear wave, f is the measured frequency of the shear wave at the location, and $\rho$ is the density of the tissue.

17. The non-transitory computer readable medium of claim 15, wherein the discrete Fourier transform component is configured to, for each location of the plural subset, calculate the instantaneous frequency from phase values within a one-dimensional window including the location.

18. A method for evaluating a biomechanical property of tissue, comprising:
   inducing a shear wave in the tissue;
   capturing an optical coherence tomography (OCT) image of the tissue;
   generating a Doppler image from the OCT image;
   determining an instantaneous frequency of the shear wave in the tissue from the Doppler image at each of a plurality of locations within the Doppler image via a discrete Fourier transform; and
   calculating a value for the biomechanical property for a plural subset of the plurality of locations from the determined frequency of the shear wave at each of the plural subset of the plurality of locations.

19. The method of claim 18, wherein inducing a shear wave in the tissue comprises inducing a shear wave in the tissue via a single shear wave source.

20. The method of claim 18, wherein determining an instantaneous frequency of the shear wave in the tissue from the Doppler image at each of a plurality of locations within the Doppler image comprising determining an instantaneous frequency of the shear wave in the tissue from the Doppler image at each of the plurality of locations from only the Doppler image and a known frequency of the induced shear wave.

* * * * *